United States Patent
Tyuluman et al.

[19]

[11] Patent Number: 5,924,073
[45] Date of Patent: Jul. 13, 1999

[54] SYSTEM AND METHOD FOR ASSESSING PHYSICIAN PERFORMANCE USING ROBUST MULTIVARIATE TECHNIQUES OF STATISTICAL ANALYSIS

[75] Inventors: Samuel A. Tyuluman; Larry P. Ammann, both of Richardson, Tex.

[73] Assignee: Beacon Patient Physician Association, LLC, Dallas, Tex.

[21] Appl. No.: 08/557,496

[22] Filed: Nov. 14, 1995

[51] Int. Cl.[6] .......................... G06F 19/00; G06F 159/00
[52] U.S. Cl. ............................. 705/2; 600/300; 705/11; 707/104
[58] Field of Search .................. 395/202, 203, 395/204, 207, 211; 705/2, 3, 4, 7, 11; 364/400; 600/300; 707/1, 104

[56] References Cited

U.S. PATENT DOCUMENTS

| | | | |
|---|---|---|---|
| 4,315,309 | 2/1982 | Coli .............................................. | 705/3 |
| 4,345,315 | 8/1982 | Cadotte et al. ......................... | 364/900 |
| 5,111,391 | 5/1992 | Fields et al. ............................. | 364/401 |
| 5,239,460 | 8/1993 | LaRoche .................................. | 364/401 |
| 5,301,105 | 4/1994 | Cummings, Jr. ........................ | 395/202 |
| 5,355,327 | 10/1994 | Stent et al. ......................... | 364/551.01 |
| 5,365,425 | 11/1994 | Torma et al. ........................... | 395/202 |
| 5,404,518 | 4/1995 | Gilbertson et al. ..................... | 395/600 |
| 5,414,621 | 5/1995 | Hough .................................... | 364/401 |
| 5,473,537 | 12/1995 | Glazer et al. ........................... | 600/300 |
| 5,544,044 | 8/1996 | Leatherman ................................ | 705/3 |
| 5,583,758 | 12/1996 | McIlroy et al. ............................. | 705/2 |
| 5,652,842 | 7/1997 | Siegrist, Jr. et al. ...................... | 705/2 |

*Primary Examiner*—Edward R. Cosimano
*Attorney, Agent, or Firm*—Baker & Botts, L.L.P.

[57] ABSTRACT

A system (10) is provided for assessing physician performance using robust multivariate techniques of statistical analysis. System (10) includes a database (14) operable to store data relating to at least one patient-physician contact. An evaluator (18) is coupled to the database (14). The evaluator (18) is operable to evaluate the data stored in the database (14) using robust multivariate techniques of statistical analysis in order to identify outliers in the data and establish a dynamic standard of care.

3 Claims, 4 Drawing Sheets

PATIENT PHYSICIAN CONTACT REGISTER

| 34 | 36 | 38 | 40 | 42 | 44 | 46 | 48 | 50 | 52 | 54 | 56 | 58 |
|---|---|---|---|---|---|---|---|---|---|---|---|---|
| DATE | PAT # | HA # | DOC # | REF DOC # | FAC | CPT | ICD0 | ICD1 | ICD2 | ICD3 | RCRS | CHG |

- DATE OF CONTACT
- PATIENT NUMBER
- HEALTH ADVISOR
- TREATING DOCTOR
- REFERRING DOCTOR
- FACILITY WHERE TREATMENT OCCURRED
- TREATMENT ADMINISTERED
- DIAGNOSIS #0
- DIAGNOSIS #1
- DIAGNOSIS #2
- DIAGNOSIS #3
- RECURSION
- CHARGE FIELD

SYSTEM AND METHOD FOR ASSESSING PHYSICIAN PERFORMANCE USING ROBUST MULTIVARIATE TECHNIQUES OF STATISTICAL ANALYSIS

TECHNICAL FIELD OF THE INVENTION

This invention relates in general to the evaluation of physician performance, and more particularly to a system and method for evaluating physician performance using robust multivariate techniques of statistical analysis.

BACKGROUND OF THE INVENTION

The rising cost of health care has generated concern among many groups. These groups have different, and very often conflicting, interests in the health care that is provided. For example, many people who receive health care services would like to be given the best medical treatment available, regardless of the cost. In other words, these people are interested only in the quality of health care. On the other hand, groups which must pay for health care, such as insurance companies, would like to maximize the medical benefits provided for a given amount of money. That is, these payers are primarily interested in the utilization of health care resources.

Ultimately, both the quality and the utilization of resources in a health care system are determined by the physicians who provide the care. Physicians who provide health care of the highest quality for the least amount of cost will be sought by both the people who receive care and the groups which pay for care. Accordingly, the conflict of interests between these groups may be resolved by evaluating the performance of physicians. In particular, comprehensive, comparative analysis of physician performance would permit normal market forces to operate in the medical marketplace so that physicians who provide high quality care for low cost are rewarded.

Prior systems and methods attempted to use classical statistical methods for analyzing physician performance. However, these prior systems and methods were frustrated by the many dimensions of data which had to be analyzed.

To begin, the individual characteristics of a patient were multivariate. Because each member of a patient population had numerous individual characteristics, classical statistical methods were unable to define a reasonable standard of care that had to be followed for the average, or "core element," of the patient population. More specifically, the classical methods did not exclude the characteristics of special patients (outliers) who did not fall within the core element. For example, one patient may have been allergic to medication that could have been used to cure a particular ailment in 99% of the patient population. This patient required a treatment that was 1000 times more expensive than the medication used on the rest of the patient population. Even though this patient was clearly an outlier, classical statistical methods did not exclude the special treatment in defining a standard of care for the core element. Consequently, the standard of care defined by classical statistics was distorted.

Furthermore, the treatment of a particular ailment was multivariate. For any particular ailment, a standard of care as described above would define the proper treatment, the expected cost of treatment, and amount of risk expected in the treatment process. A physician who did not administer proper treatment, charged an abnormally high rate for the treatment, or exposed a patient to a greater amount of risk than necessary in treatment was considered to be performing outside of the standard of care. Although such a physician should have been identified by comparative analysis, classical statistical methods were often unable to do so.

Accordingly, a need has arisen for a system and method to accurately assess the comparative performance of a physician.

SUMMARY OF THE INVENTION

In accordance with the teachings of the present invention, the disadvantages and problems associated with previous methods and systems used to evaluate the performance of a physician have been substantially reduced or eliminated. The present invention provides a system and method for evaluating the performance of a physician using robust multivariate techniques of statistical analysis.

According to one embodiment of the present invention, a system is provided for assessing physician performance. The system includes a database operable to store data relating to a patient-physician contact. An evaluator is coupled to the database. The evaluator is operable to evaluate the data stored in the database using robust multivariate techniques of statistical analysis.

According to another embodiment of the present invention, a method is provided for assessing physician performance. The method includes a plurality of steps. Those steps are: collecting data relating to a patient-physician contact; storing the data in a database; and evaluating the data stored in the database using robust multivariate techniques of statistical analysis.

According to yet another embodiment of the present invention, a method is provided for assessing the ability of a physician to efficiently diagnosis an ailment. The method includes a plurality of steps. Those steps are: generating a plurality of transition probabilities; generating a probable transition sequence from the transition probabilities; generating at least one data unit from a patient-physician contact, the data unit comprising information relating to a single diagnosis and the characteristics of the patient; from the data units generated, reconstructing an actual transition sequence of diagnoses given by the physician before diagnosing the ailment; determining whether the actual transition sequence is the same as the probable transition sequence; informing a physician that he is performing in accordance with the established standard of care if the actual transition sequence is the same as the probable transition sequence; analyzing the actual transition sequence using multivariate techniques to determine whether the actual transition sequence is more efficient than the probable transition sequence; setting the probable transition sequence to the actual transition sequence to establish a higher standard of care, if the actual transition sequence is more efficient; and informing the physician that he is not performing in accordance with the reasonable standard of care, if the actual transition sequence is less efficient.

An important technical advantage of the present invention is the use of robust multivariate techniques of statistical analysis to assess the performance of a physician. Another important technical advantage of the present invention is that a standard of care may be defined for a core element of a patient population. Yet another important technical advantage of the present invention is the identification of patients who do not fall within the core element. Yet another important technical advantage of the present invention is that physicians who perform outside of the standard of care can be identified. Yet another important technical advantage of the present invention is that the standard of care may be updated based upon the identification of more efficient and more effective treatments. Yet another important technical advantage of the present invention is that fewer doctors need to be individually scrutinized, thereby reducing the cost associated with monitoring doctors. Yet another important advantage is the ability to assess the diagnostic efficiency of individual physicians.

BRIEF DESCRIPTION OF THE DRAWINGS

For a more complete understanding of the present invention and for further features and advantages, reference is now made to the following description taking in conjunction with the accompanying drawings, wherein like reference numerals represent like parts, in which.

DETAILED DESCRIPTION OF THE INVENTION

The preferred embodiment of the present invention and its advantages are best understood by referring to FIGS. 1–5 of the drawings, like numerals being used for like and corresponding parts of the various drawings.

The treatment, outcome, and cost of treating a particular ailment for a patient population of individuals with comparable physical attributes and medical conditions should be very similar. In accordance with the present invention, a system and method are provided to accomplish several objectives. One objective is to define a standard of care for the core element of a patient population. Another objective of the present invention is to identify ineffective or inefficient treatment of patients by a physician.

Classical statistical methods are unable to accomplish either objective for two reasons. First, the information that must be analyzed is multivariate in nature. In other words, the information includes many variables, each of which must be considered in the analysis. Second, the information to be studied includes outliers. Outliers are special cases which distort the analysis because they deviate so far from the average or core element. Outliers have a masking effect. Because it is relatively easy to identify gross outliers that are far from the core element, these gross outliers can be individually excluded from the information that is analyzed. Other outliers, however, may be included in the analysis because they do not seem as severe as the gross outliers. Consequently, the analysis of data using classical techniques is distorted.

Robust multivariate techniques of statistical analysis are far superior to classical techniques for analyzing this type of data. As stated above, one objective of the present invention is to establish a standard of care for the treatment of an ailment within a core element of the patient population. The analysis is multivariate or multidimensional in the sense that many factors are considered. The analysis is robust in the sense that outliers in the patient population are identified, so they can be excluded when the standard of care is calculated. In other words, individuals having characteristics that differ greatly from the core element are excluded when formulating the statistical representation. The standard is considered "dynamic" in that it is being continually updated with current information. This robust standard of care may define the proper spectrum of treatments, cost of treatments, and amount of risk involved in the treatment of an ailment for the core element.

Another aspect of the present invention is to identify ineffective or inefficient treatment of patients. Once a robust standard of care for the treatment of an ailment has been established, the method and system will identify as performing outside that standard any physician who does not administer proper treatment, charges an abnormally high rate for the treatment, or exposes a patient to a greater amount of risk than necessary in treatment. Such a physician is considered to be an outlier since he or she does not adhere to the established standard of care.

Accordingly, the present invention provides a system and method for assessing the performance of a physician using time-based, robust multivariate techniques of statistical analysis. The system and method provide comprehensive comparative physician performance data to practitioners, patients, and payers alike. In essence, the comprehensive comparative physician performance data is a medical consumer report.

Figure 1:
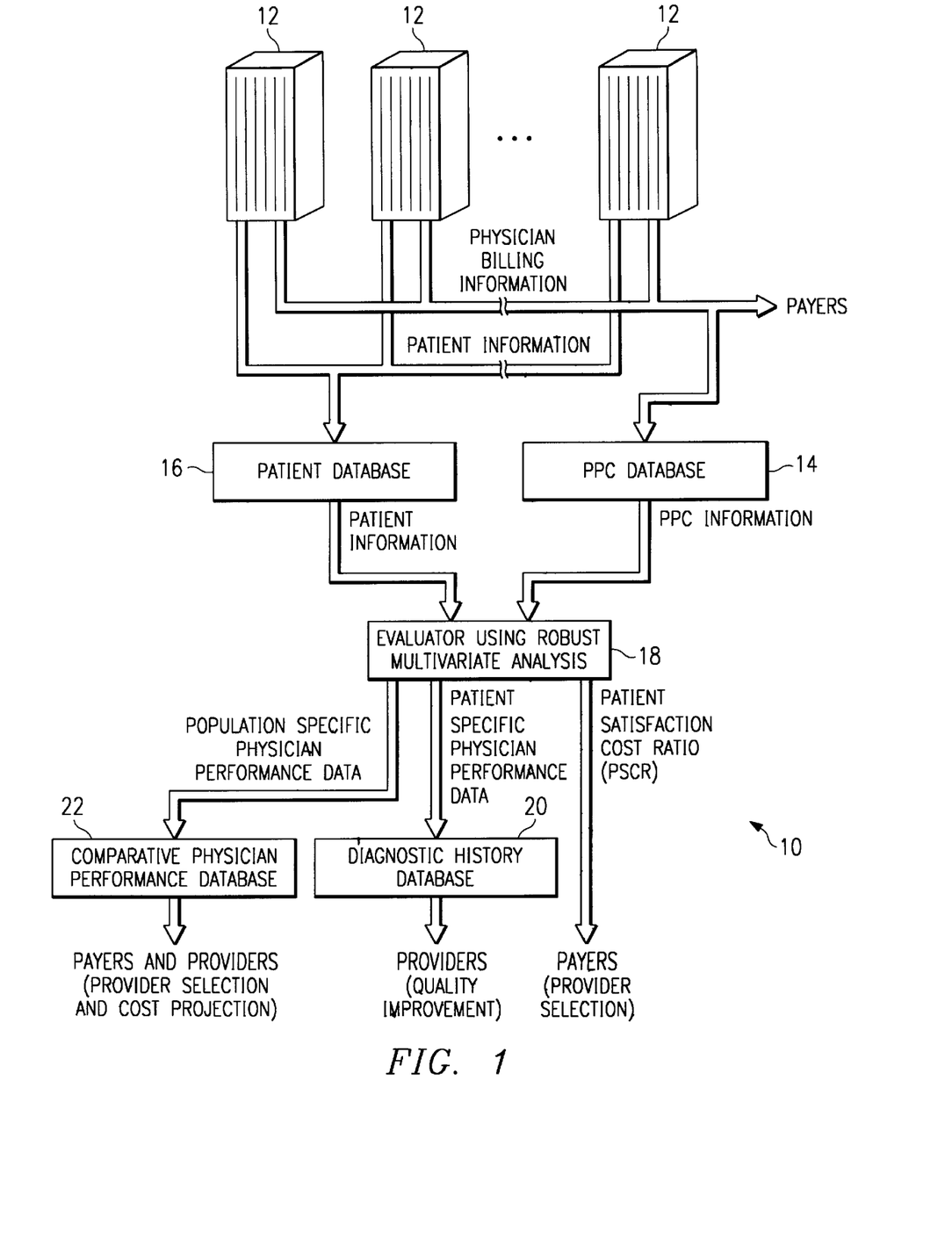
FIG. 1 illustrates a system for assessing the physician performance using robust multivariate techniques of statistical analysis according to a preferred embodiment of the present invention.

FIG. 1 illustrates a system 10 for assessing physician performance using time-based, robust multivariate techniques of statistical analysis, according to a preferred embodiment of the present invention. In system 10, patients receive health care services at a plurality of health care facilities 12. More particularly, patients meet with physicians at a facility 12 to receive treatment for their ailments. During this meeting or contact between the patient and the physician, the physician examines the patient to determine what ails the patient. The physician makes one or more diagnoses based upon the examination. For each diagnosis the physician may administer, or order to be administered, a corresponding treatment.

Subsequent to the contact between the patient and the physician, facility 12 generates billing information based upon the services ordered by the physician and provided to the patient. The billing information is sent to the payer of the services. This payer may be the patient or a third party, such as an insurance company. The billing information contains a variety of information, such as the identity of the patient, the identity of the treating doctor, the identity of a referring doctor (if any), the date of the patient-physician contact, the diagnoses given by the treating doctor, the treatment administered, the cost, and the amount of facility usage ordered by the physician.

Referring to FIG. 1, information generated at the contact between the patient and the physician may be extracted from the billing information. A patient-physician contact is defined as a dated diagnosis/treatment pair associated with identifying data such as patient number, facility, and referring physician. The patient-physician contacts collectively are referred to as patient-physician contact (PPC) information. A patient-physician contact (PPC) database 14 is used to store the PPC information.

The facility 12 also generates and maintains information about each of its patients ("patient information"). The patient information relates in part to the characteristics of each patient, such as age, height, weight, sex, allergies, race, and coexisting ailments (comorbidities). In system 10, such confidential patient information may be collected from the facilities 12 and securely stored using encryption techniques in a patient database 16. FIG. 1 illustrates that patient database 16 is separate from PPC database 14. Alternatively, patient database 16 and PPC database 14 may be combined in a single, larger database.

An evaluator 18 is connected to patient database 16 and PPC database 14. Evaluator 18 may include one or more processing units and associated support memories for analyzing data. In a preferred embodiment, evaluator 18 includes a plurality of processing units in which different groups of processing units perform different functions. Within each group, a main processing unit and several backup processing units are provided. If the main processing unit fails, the backup units take over the processing functions. Furthermore, the failure of an entire group does not effect the performance of the other groups. Accordingly, evaluator 18 may have built-in fault tolerance.

Evaluator 18 receives patient information from patient database 16 and PPC information from PPC database 14. Evaluator 18 may generate one or more data units from the patient information and the PPC information. A data unit is associated with the clinical course of a single patient. Consequently, a data unit identifier will include a unique patient identifier. Each data unit also may include facility utilization information and specialist referral information. Each data unit is associated with a single diagnostic code. More specifically, during any given contact between a patient and a physician, the physician may render one or more diagnoses. Testing in response to a first diagnosis may lead the physician to render another diagnosis. Consequently, a chain of related diagnoses may be generated during a single contact between a patient and physician. This chain of diagnoses may be represented by the following:

$$D_{X1} \rightarrow D_{X2} \rightarrow D_{X3} \rightarrow D_{X4} \rightarrow D_{X5} \ldots D_{Xn}$$

where $D_{X1}$, $D_{X2}$, $D_{X3}$, $D_{X4}$, $D_{X5}$, and $D_{Xn}$ symbolize a series of diagnoses. $D_{Xn}$ represents the diagnosis of the patient's ailment.

Evaluator 18 uses time-based robust multivariate techniques of statistical analysis to evaluate the received data or the data units. Robust techniques are designed to identify a location parameter of a population of measurements in such a way that the presence of an outlying minority of observations does not unduly influence that identification. In other words, the location parameter is not distorted by anomalies. Two benefits are achieved with this technique: ① identification of the location parameter of the main core of the population of measurements, and ② identification of outliers.

Consequently, these techniques may be employed to define a standard of care for an ailment within the core element of a patient population. The standard of care may encompass a treatment, cost of treatment, relative risk of treatment, and outcome of treatment for an ailment. In deriving the standard of care, evaluator 18 robustly identifies the core element of data units. Data units with characteristics that differ significantly from the core element are considered to be outliers.

The patient-physician contact information and patient information received by evaluator 18 allows the evaluator to properly account for the individual differences between patients. Some individual differences are significant in determining how a particular patient should be considered in defining the standard of care. Other individual differences are not important.

For example, a patient's allergic reaction to a popular drug should be considered in deciding the standard of care for an ailment that is readily cured by the drug. This patient constitutes an outlier, and accordingly, his or her characteristics should be excluded from the analysis. Consequently, any treatment provided to the outlier, fee charged for the treatment, or risk to which the outlier is exposed will not be considered in defining the respective aspect of the standard of care.

On the other hand, the same allergic reaction would not be considered important in deciding the standard of care for a broken limb, which cannot be treated by the drug. The patient is not considered an outlier in this case. Consequently, his or her patient information can be used in defining the standard of care for treatment of a broken limb. Evaluator 18 statistically analyzes this information to determine how differences in treatment, outcome of treatment, and cost associated with a diagnosis or diagnostic group depend upon the physician, the characteristics of the patient, and the co-morbidity of the patient. Analysis of the information at the level of the contact between patient and physician enables the development of a dynamic standard of care for the treatment of ailments.

The analysis for defining a standard of care is designed to identify components of patient care which are more costly to implement, have greater risk exposure, or include ineffective treatment, compared to methods that attain the same or better results for a patient. Accordingly, system 10 provides a representation of the robust standard of care that should be followed based on the characteristics of a particular patient.

Furthermore, robust multivariate techniques are also used to identify physicians who practice outside the standard of care. This line of analysis is important for two reasons.

First, the system 10 can identify physicians who perform outside the standard of care. These are physicians who provide incorrect or unnecessary treatment, charge excessive amounts for treatment, or expose a patient to more risk than necessary during treatment. For example, some physicians may perform many unnecessary tests in order to collect more money from the payer of health care. These physicians should be identified. Because most physicians do not perform unnecessary tests, the cost associated with monitoring the physicians will be greatly reduced by the computerized system described. It should be noted that physicians who treat special cases, such as high-risk patients, will not be penalized in the assessment of their performance, because the robust multivariate techniques recognize these special cases when analyzing the physician's performance.

Second, system 10 identifies those physicians who perform above the standard of care. Physicians who are able to deliver the same or better treatment with significantly lower cost or less exposure to risk will be identified as performing above the standard of care. These physicians may have developed a better procedure that is more efficient or effective than the current standard of care. The methods of these physicians can be evaluated and made available to the health care community. The standard of care is progressively and automatically redefined so that the overall quality and cost of care is improved.

Still referring to FIG. 1, evaluator 18 may output one or more results after analyzing the data it receives using robust statistical techniques. The results are somewhat viewer-specific in that certain results are important only to certain groups. The results are broadly defined as patient satisfaction cost ratio (PSCR) and physician performance data.

Evaluator 18 outputs a PSCR to the payers of the health care provided and the consumers of health care services. The PSCR is intended to give health advisors, consumers, and payers some quantitative measure of the overall performance and cost of a specific physician. The breakdown of the PSCR also provides physicians with feedback concerning their relative performance. In a preferred embodiment, the PSCR is a single number on a scale of 0.0 to 5.0 that may be used by payers to assess a physician, and by physicians to assess a specialist or a facility. The PSCR takes into account four variables associated with every patient-physician contact. These variables are cost, risk, outcome, and satisfaction.

To measure relative cost in a preferred embodiment, all treatments are ranked by cost and placed on a scale from 0 to 100. The costliest treatments appear at the upper end of the scale. During every calendar quarter, all diagnostic groups in which a physician is active are summed and normalized to produce relative mean cost ($C_{RM}$). $C_{RM}$ is a number representing total running relative cost of treatment for a diagnostic group. $C_{RM}$ is calculated as follows:

$$C_{RM} = \sum_{Pt=1}^{X} \sum_{t=0}^{T} CPTCost(t, Pt)$$

where Pt is a given patient, X is the total number of patients treated, t is time, T is the end of the quarter, and CPTCost is the total cost of treatment from the onset of diagnosis (i.e., t=0). Robust techniques are utilized to insure that patient outliers do not have an adverse impact on the calculation of these variables. These techniques produce a robust standard for $C_{RM}$. The deviance of individual physicians from this standard represents a measure of individual physician cost performance.

To measure relative risk, all treatments are ranked by their relative risk on a scale from −10 to +10. A board of physicians may determine the rankings. The treatments having the highest risk appear at the upper end of the scale. It should be noted that some treatments reduce risk. Consequently, these treatments are assigned a negative number. In this manner, the risk associated with a diagnosis or diagnostic group can be calculated. Thus, a balance between the risk of treatment a patient is exposed to and the risk associated with a corresponding diagnosis can be made. Treating risk in this fashion promotes the use of preventive medicine, such as inoculations, mammograms, cholesterol screening, without adversely affecting the physician PSCR. All diagnostic groups in which the physician is active are summed and normalized to produce relative mean risk ($R_{RM}$). $R_{RM}$ is a number representing total running relative risk of treatment for a diagnostic group. Robust techniques are used to insure that patient outliers do not have an adverse impact on these calculations. These techniques produce a robust standard for $R_{RM}$. The deviance of $R_{RM}$ from this standard represents a measure of individual physician risk performance.

To measure relative outcome, a patient's response to a given treatment is ranked on a scale of −10 to +10. If a patient's condition improves, the outcome is ranked with a high number. If a patient's condition worsens, the outcome is ranked with a low or negative number. All outcomes for a physician are accumulated, normalized and scaled to produce relative mean outcome ($O_{RM}$). $O_{RM}$ is a number representing total running relative outcome of treatment for a diagnostic group. Robust techniques are used to insure that patient outliers do not have an adverse impact on these calculations. These techniques produce a robust standard for $O_{RM}$. The deviance of $O_{RM}$ from this standard represents a measure of individual physician outcome performance.

To measure relative satisfaction, patients are asked to complete a satisfaction survey, based on symptoms and diagnosis, ranking their physician's treatment. All responses to satisfaction surveys are accumulated for a physician, normalized and placed on a scale of 1 to 100 to produce relative mean satisfaction ($S_{RM}$). $S_{RM}$ m is a number representing total running relative satisfaction of treatment for a diagnostic group. Robust techniques are used to insure that patient outliers do not have an adverse impact on these calculations. These techniques produce a robust standard for $S_{RM}$. The deviance of $S_{RM}$ from this standard represents a measure of individual physician satisfaction performance.

Using the above-calculated numbers for $C_{RM}$, $R_{RM}$, $O_{RM}$, and $S_{RM}$, PSCR may be calculated as follows:

$$PSCR = (S_{RM} + O_{RM}) - (C_{RM} + R_{RM}) \qquad (1)$$

Alternatively, PSCR may be calculated as follows:

$$PSCR = \frac{S_{RM} + O_{RM}}{C_{RM} + R_{RM}} \qquad (2)$$

The PSCR value in equation (1) does not fluctuate with changes in $S_{RM}$, $O_{RM}$, $C_{RM}$, and $R_{RM}$ as severely as the PSCR value in equation (2). It should be noted that $S_{RM}$, $O_{RM}$, $C_{RM}$, $R_{RM}$ are assigned equal weights in both equation (1) and equation (2). The physician will receive a quarterly report which details the above calculation. In this way, payers are able to assess which physicians provide the most satisfactory service to a patient population.

In addition to PSCR, evaluator 18 also outputs patient specific physician performance data. This data may be stored in a diagnostic history database 20. The patient specific physician performance data may include information relating to a physician's ability to efficiently assess and treat an ailment. The patient specific patient physician performance data may be sent to providers of health care so that the providers may inform their physicians about their performance. The patient specific physician performance data identifies individual patients treated by a physician. Because the patient specific physician performance data may contain information that is confidential to a patient, the patient specific physician performance data should not be available to the payers of health care.

With further reference to FIG. 1, evaluator 18 also outputs population specific physician performance data. Population specific physician performance data may be stored in comparative physician performance database 22. Population specific physician performance data includes information relating to different populations of patients having similar characteristics. Unlike the patient specific physician performance data stored in diagnostic history database 20, the population specific physician performance data does not reveal the identity of individual patients treated by a physician. Accordingly, this information may be sent to both the payers and providers of health care. The payers and providers may use the information to project future costs of health care for patients. The payers of health care may use the information to select providers in the future.

Diagnostic history database 20 and physician performance database 22 are shown as being separate from patient database 16 and PPC database 14. In other embodiments, however, all four databases may be combined in a single, larger database.

Figure 2:
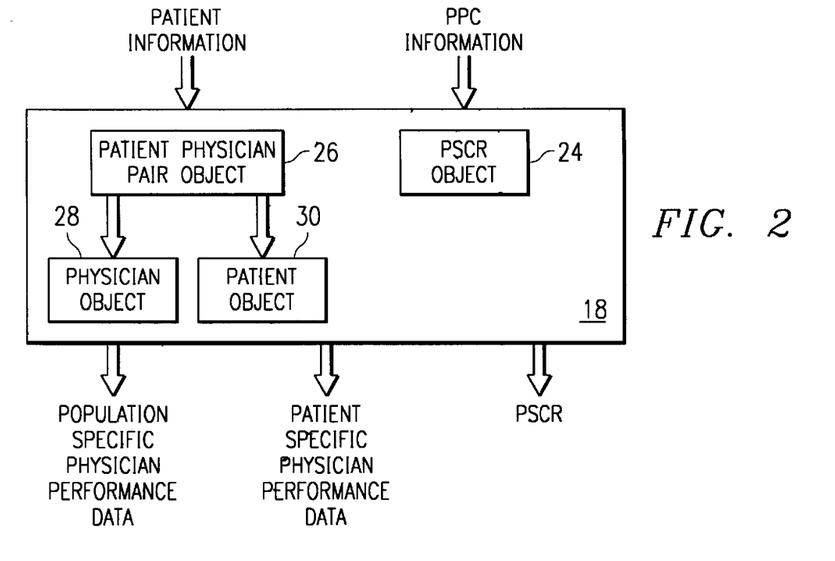
FIG. 2 illustrates the details of an evaluator shown in FIG. 1 according to the preferred embodiment of the present invention.

FIG. 2 illustrates the details of evaluator 18 shown in FIG. 1, according to the preferred embodiment of the present invention. Evaluator 18 includes a patient satisfaction cost ration (PSCR) object 24, a patient physician pair (PPP) object 26, a physician object 28, and a patient object 30. Evaluator 18 generates the numerical value for PSCR, as well as precise comparative physician evaluations and data to facilitate the projections of cost for a given set of patient characteristics.

PSCR object 24 is a computer program. PSCR object 24 receives the PPC information. Using the PPC information, PSCR object 24 generates the PSCR number as described above.

PPP object 26 is a computer program that accesses the PPC information and patient information. The PPP object organizes this information in order to establish a robust standard of care on a diagnosis by diagnosis basis. The treatment of a diagnosis is referenced to a time line based on a Julian calendar date of 1850. The onset of the diagnosis is then defined to be the date of the first treatment. The time course of treatment referenced to the onset of diagnosis for each physician patient pair can be compared for any diagnosis or diagnostic group. PPP object 26 establishes a robust time-based standard of care on a diagnosis by diagnosis basis for the following: (1) absolute cost of treatment using the fee actually charged, (2) relative cost treatment using a base fee schedule, (3) risk of treatment based on available mortality and morbidity data, and (4) probability that a diagnosis will remain unchanged once the diagnosis has been made ("diagnostic stability").

Physician object 28 is a computer program which establishes a robust multivariate fit of an individual physician's treatment patterns for a diagnosis or diagnostic group. Physician object 28 compares the individual physician to the robust standard by diagnosis or diagnostic group. Comparisons are made of the following: (1) relative cost deviance, (2) absolute cost deviance, (3) risk deviance, (4) deviance in time rate of relative cost, (5) deviance in time rate of absolute cost, (6) deviance in time rate of risk, and (7) deviance of diagnostic stability. These measures of deviance may be given to payers, patients, and providers without compromising patient confidentiality. Additional comparisons are performed on the patterns of treatments used by a physician for a diagnosis or diagnostic group. For any given diagnosis, physician object 28 generates a spectrum of known treatments. An individual physician's choice of treatments for that diagnosis or diagnostic group is robustly compared to the patterns created by other practitioners. Physician object 28 calculates the deviance using robust multivariate techniques and then provides the calculated deviances to payers, physicians, and patients.

Like the other objects in evaluator 18, patient object 30 is a computer program. Patient object 30 uses the data organized by PPP object 26 to analyze patient care parameters. Patient object 30 is time-based. Patient object 30 is useful for developing access and availability profiles for a provider and for the projection of future cost of care for a patient population. Several calculations can be used to predict the future cost of care and the value of preventive care for a patient population. Again, robust multivariate techniques must be used to obtain a useful assessment of the projected cost and value of care delivered to a given patient population. Calculations made by patient object 30 include the following: (1) relative cost of a diagnosis or diagnostic group, (2) absolute cost of a diagnosis or diagnostic group, (3) risk associated with a diagnosis or diagnostic group, (4) time rate of relative cost, (5) time rate of absolute cost, (6) time rate of risk, and (7) expected diagnostic stability. Patient object 30 significantly reduces or eliminates the errors inherent in standard actuarial techniques for the prediction of future cost of care and it allows a more accurate assessment of the value of preventive care.

Figure 3:
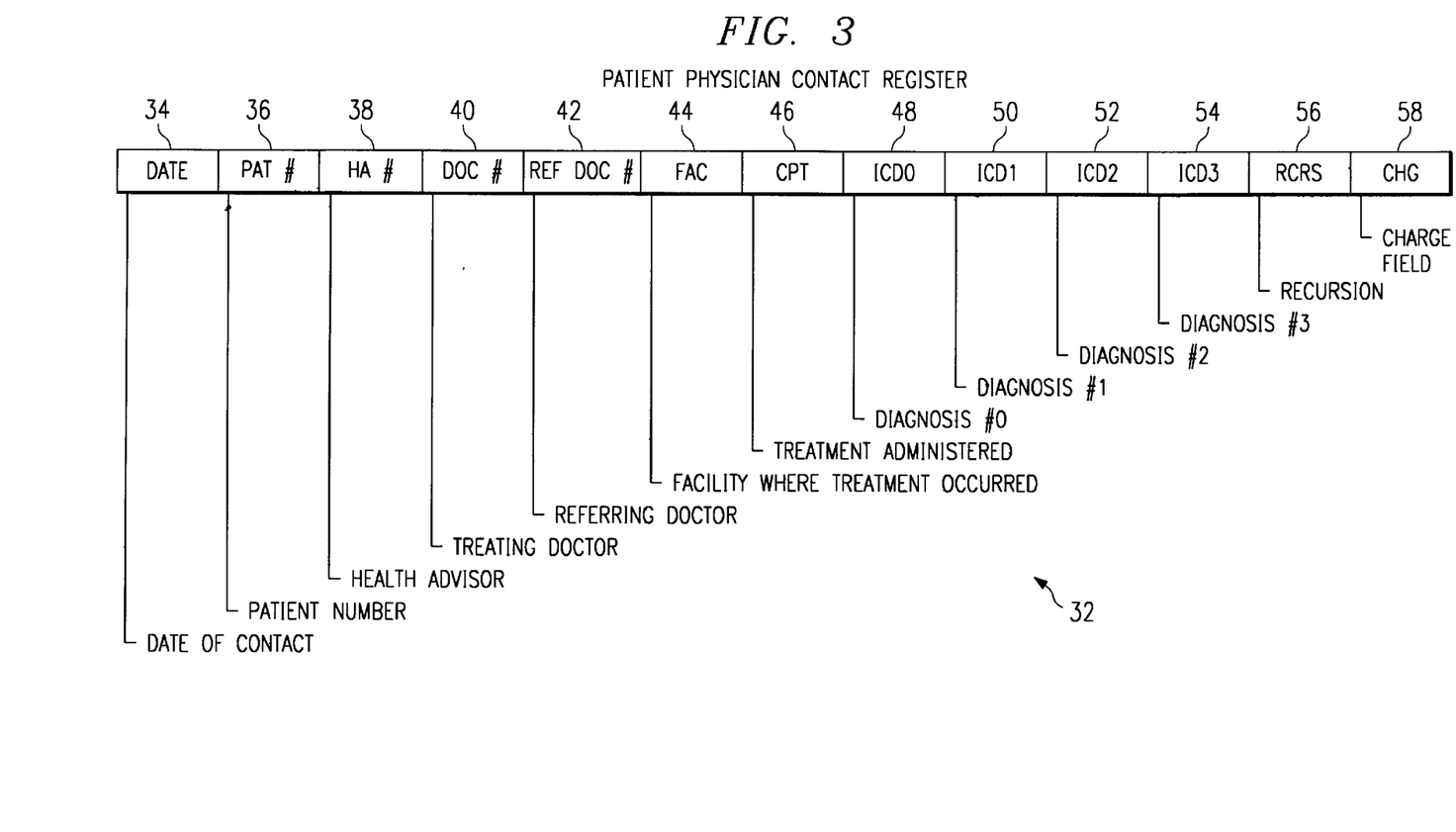
FIG. 3 illustrates a patient-physician contact register according to a preferred embodiment of the present invention.

FIG. 3 illustrates a patient-physician contact (PPC) register 32. PPC register 32 may be included in PPC database 14. PPC register 32 contains information relating to a plurality of contacts between patients and physicians. The information is arranged according each contact between a patient and a physician. Each entry in PPC register 32 includes a plurality of information relating to a specific contact. As shown in FIG. 3, PPC register 32 includes a date register 34 which stores the date of a specific contact. A patient number register 36 stores the identification of a patient. A health advisor register number 38 contains the name of the physician who is directing the patient case. A treating doctor number register 40 and a referring doctor number register 42 contain the names of the doctor administering treatment and the doctor, if any, who referred the patient to the treating doctor, respectively. A facility register 44 contains the identity of the facility where treatment occurred. A CPT register 46 contains a current procedural terminology (CPT) code identifying the treatment administered. An ICDO register 48 contains the international classification of diseases (ICD) code of a first diagnosis by the treating doctor. An ICD1 register 50 contains the ICD code of a second diagnosis. An ICD2 register 52 contains the ICD code of a third diagnosis. Likewise, ICD3 register 54 contains the ICD code for a fourth diagnosis. An RCRS register 56 contains a recursion field which is used to track diagnostic accuracy. Diagnostic accuracy is the ability of a physician to accurately diagnosis an ailment. A CHG register 58 contains the amount charged for the treatment.

Figure 4:
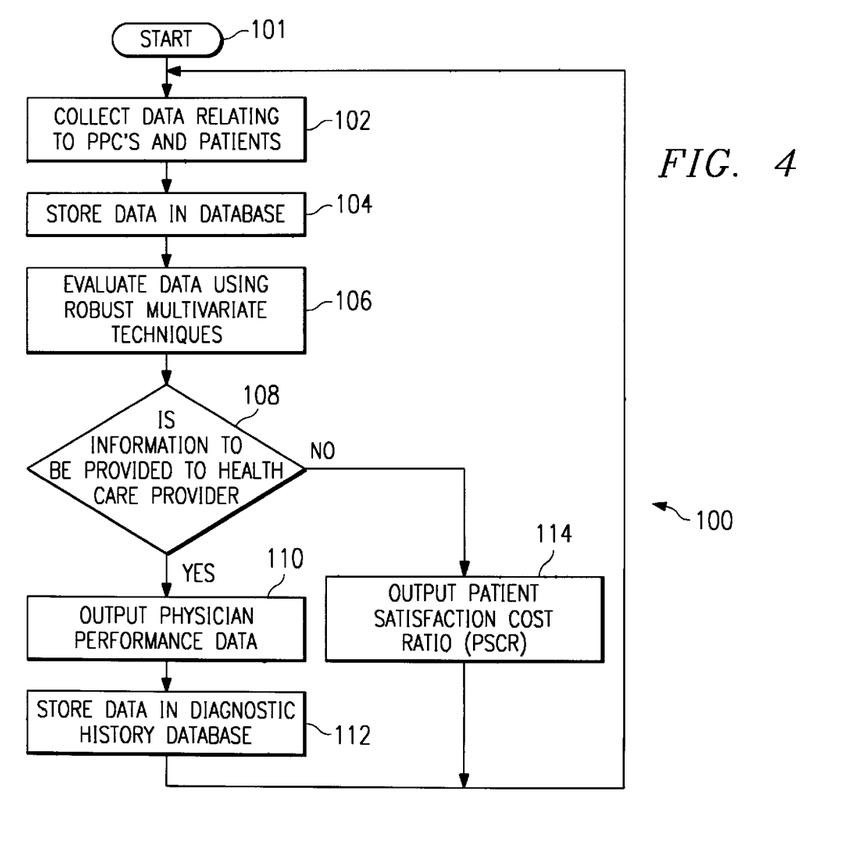
FIG. 4 is a flow diagram that illustrates a method for assessing physician performance using robust multivariate techniques of statistical analysis according to a preferred embodiment of the present invention.

FIG. 4 is a flow diagram that illustrates a method 100 for assessing physician performance according to a preferred embodiment of the present invention. Method 100 describes the operation of system 10 shown in FIG. 1. Consequently, method 100 is best understood with reference to FIGS. 1 and 4.

At step 101, method 100 is started. At step 102, data relating to PPCs and patients is collected from a plurality of health care facilities 12. The PPC data may be extracted from patient billing information that is provided to the payers of health care services. The patient data is received from one or more facilities 12. At step 104, the collected data may be stored in one or more databases, such as PPC database 14 and patient database 16.

An evaluator 18 receives information stored in PPC database 14 and patient database 16. At step 106, evaluator 18 evaluates the data using time-based robust multivariate techniques of statistical analysis. As described above, the robust multivariate analysis is used to output a number of things. The present invention contemplates that primarily three groups are concerned about the output information: health care providers, patients, and payers of health care services. The output of evaluator 18 will depend upon which group or groups will be receiving information. It must be understood, however, that all information output by evaluator 18 can be made available to all groups. In addition, other privileged parties may be given access to the output information in some instances.

At step 108, it must be decided whether the information output by evaluator 18 is to be provided to a health care provider. If the information is to be provided to a health care provider, then evaluator 18 outputs physician performance data at step 110. Physician performance data is supplied to the provider on a diagnosis by diagnosis basis. Each physician can then assess, on a diagnosis by diagnosis basis, his/her deviation from the standards for relative performance in terms of cost, risk, satisfaction, and outcome. Because robust multivariate methods are utilized, outliers do not distort the relative measures of physician performance. The health care provider is able to provide feedback and constructive criticism of a physician's performance using the physician performance data. At step 112 the physician performance data is stored in diagnostic history database 20.

On the other hand, if it is determined that the information is not to be provided to a health care provider, evaluator 18 outputs information to the remaining two groups: the patients and the payers of health care services. This output information includes a patient satisfaction cost ratio (PSCR) at step 114. Other patients and payers of health care services may use the PSCR in deciding whether to seek medical treatment from a particular physician or health care provider. In this way, market forces are able to compensate physicians who provide exceptional care. Likewise, market forces will force inefficient or poorly performing physicians to either improve their cost efficiency or improve their performance. Process 100 returns to step 102.

Figure 5:
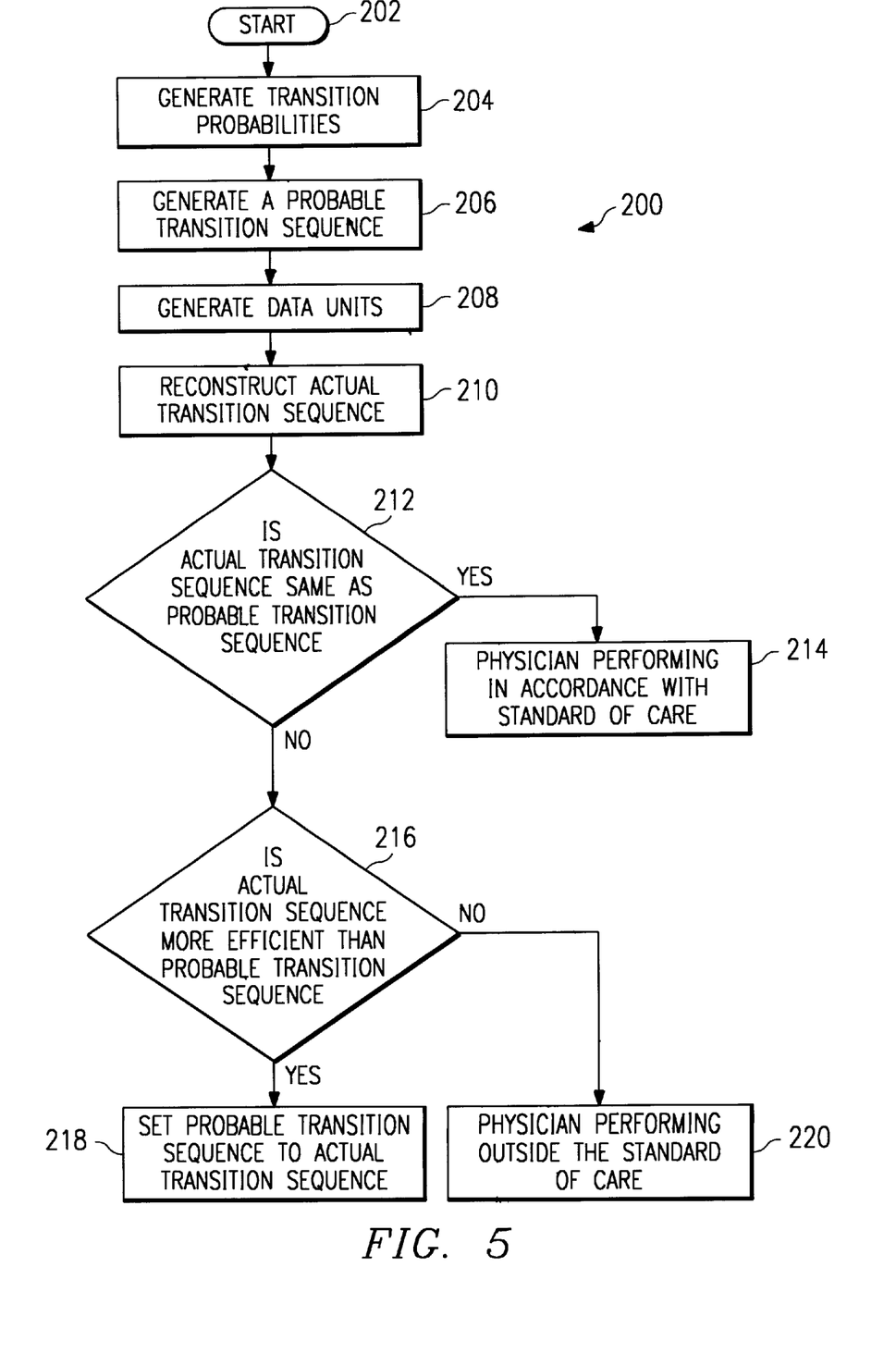
FIG. 5 is a flow diagram that illustrates a method for assessing the ability of a physician to efficiently diagnose an ailment according to a preferred embodiment of the present invention.

FIG. 5 is a flow diagram that illustrates a method 200 for assessing the ability of a physician to efficiently diagnosis an ailment according to a preferred embodiment of the present invention. Method 200 is related to method 100 described above with reference to FIG. 4. More particularly, method 200 outputs one form of physician performance data. Like method 100, method 200 describes an operation of system 10 shown in FIG. 1. Accordingly, method 200 is best understood with reference to FIGS. 1 and 5.

At step 202, method 200 is started. At step 204, evaluator 18 generates a plurality of transition probabilities. More specifically, for some ailments, a physician may not be able to render a correct diagnosis immediately. Rather, the physician follows an iterative process in which the physician gives a diagnosis, treats for the diagnosed ailment, changes the diagnosis based on the response to treatment or a diagnostic test, treats for next diagnosis, and so on. A transition probability is defined as the relative frequency with which physicians make a transition from one diagnosis to another.

At step 206, method 200 generates a probable transition sequence from the transition probabilities. The probable transition sequence establishes a standard of care. In other words, the probable transition sequence comprises a plurality of diagnoses which may be given before diagnosing the ailment. The sequence of diagnoses should not be haphazard, but rather each diagnosis should logically follow from the preceding diagnosis. The iteration of the steps of diagnosing and testing is continued until there is a substantial likelihood that the physician would render the final diagnosis. At this point, the physician is considered to have reached "diagnostic stability." The "diagnostic efficiency" of a physician for a particular ailment is defined as the time and cost required for the physician to reach diagnostic stability. The history of these diagnostic transitions is available in a database. The collection of transition probabilities for all diagnosis is used to define a standard of diagnostic efficiency for all physicians. The performance of an individual physician can be compared to this standard.

At step 208, a plurality of data units is generated from a contact between a patient and a physician. This contact may occur at a facility 12. The data units may include information relating to a single diagnosis and the characteristics of the patient.

At step 210, method 200 reconstructs an actual transition sequence of diagnoses from the data units generated. The actual transition sequence represents all the diagnoses given by the physician before diagnosing the patient's ailment.

At step 212, evaluator 18 determines whether the actual transition sequence is the same as the probable transition sequence, which was previously generated. If the actual transition sequence is the same as the probable transition sequence, then at step 214, method 200 informs the physician that he or she is performing in accordance with the established standard of care.

If the actual transition sequence is not the same as the probable transition sequence, then at step 216, evaluator 18 analyzes the actual transition sequence using multivariate techniques to determine whether the actual transition sequence is more efficient than the probable transition sequence.

At step 218, if the actual transition sequence is more efficient, method 200 sets the probable transition sequence to the actual transition sequence to establish a higher standard of care.

On the other hand, if the actual transition sequence is less efficient than the probable transition sequence, method 220 informs the physician that he is performing outside the standard of care.

Although the present invention and its advantages have been described in detail, it should be understood that various changes, substitutions and alterations can be made herein without departing from the spirit and scope of the invention as defined by the appended claims.

What is claimed is:

1. A method for assessing data associated with physician performance using robust multivariate techniques of statistical analysis comprising:

collecting data relating to a patient physician contact;

storing the data in a database;

generating a plurality of data units from the patient-physician contact, each data unit comprising information relating to a single diagnosis and the characteristics of the patient;

identifying all data units in which a diagnosis for an ailment was given;

categorizing by ailment the data units in which a diagnosis was given;

associating the data units in which a correct diagnosis was not given with one of the data units in which a correct diagnosis was given, thereby categorizing all data units by ailment; and, analyzing all data units relating to a particular ailment using robust multivariate techniques in order to establish a probable transition sequence comprising a plurality of diagnoses which may be given before diagnosing the ailment, the probable transition sequence defining the standard of care for the treatment of that ailment.

2. A method for assessing the ability of a physician to efficiently diagnose an ailment, comprising the steps of:

generating a plurality of transition probabilities;

generating a probable transition sequence from the transition probabilities;

generating at least one data unit from a patient-physician contact, the data unit comprising information relating to a single diagnosis and the characteristics of the patient;

from the data units generated, reconstructing an actual transition sequence of diagnoses given by the physician before diagnosing the ailment;

determining whether the actual transition sequence is the same as the probable transition sequence;

informing a physician that he is performing in accordance with the established standard of care if the actual transition sequence is the same as the probable transition sequence;

analyzing the actual transition sequence using multivariate techniques to determine whether the actual transition sequence is more efficient than the probable transition sequence;

setting the probable transition sequence to the actual transition sequence to establish a higher standard of care, if the actual transition sequence is more efficient; and informing the physician that he is not performing in accordance with the reasonable standard of care, if the actual transition sequence is less efficient.

3. The method of claim 2, wherein the step of generating a probable transition sequence comprises the step of generating a plurality of diagnoses which may be given before diagnosing the ailment.

* * * * *